(12) United States Patent
Martinez

(10) Patent No.: US 7,424,929 B1
(45) Date of Patent: Sep. 16, 2008

(54) COVER FOR A BELL OR A DIAPHRAGM OF A STETHOSCOPE

(75) Inventor: Richard Martinez, Algonquin, IL (US)

(73) Assignee: Stethocap, Inc., Rolling Meadows, IL (US)

( * ) Notice: Subject to any disclaimer, the term of this patent is extended or adjusted under 35 U.S.C. 154(b) by 407 days.

(21) Appl. No.: 11/232,711

(22) Filed: Sep. 22, 2005

(51) Int. Cl.
*A61B 7/02* (2006.01)
*A61B 7/00* (2006.01)

(52) U.S. Cl. ..................................... 181/131

(58) Field of Classification Search ................ 181/131; 600/528; 381/67; D24/134
See application file for complete search history.

(56) References Cited

U.S. PATENT DOCUMENTS

| | | | |
|---|---|---|---|
| 3,255,841 A | 6/1966 | Hasbrouck | |
| 3,276,536 A * | 10/1966 | Littmann | 181/137 |
| 3,470,975 A * | 10/1969 | Haiken | 181/131 |
| 3,601,218 A * | 8/1971 | Reynolds | 181/137 |
| 4,461,368 A | 7/1984 | Plourde | |
| 4,475,619 A * | 10/1984 | Packard | 181/137 |
| 4,867,265 A * | 9/1989 | Wright | 181/131 |
| 4,867,268 A * | 9/1989 | Ulert | 181/137 |
| 4,871,046 A | 10/1989 | Turner | |
| 4,995,473 A | 2/1991 | Packard | |
| 5,269,314 A * | 12/1993 | Kendall et al. | 600/528 |
| 5,365,023 A | 11/1994 | Lawton | |
| 5,424,495 A | 6/1995 | Wurzburger | |
| 5,428,193 A | 6/1995 | Mandiberg | |
| 5,448,025 A * | 9/1995 | Stark et al. | 181/131 |
| 5,466,897 A | 11/1995 | Ross et al. | |
| 5,528,004 A | 6/1996 | Wurzburger | |
| 5,564,431 A * | 10/1996 | Seward | 600/528 |
| 5,587,561 A * | 12/1996 | Budayr et al. | 181/131 |
| 5,599,093 A | 2/1997 | Hoftman et al. | |
| 5,686,706 A | 11/1997 | Wurzburger | |
| 5,747,751 A | 5/1998 | Weckerle | |
| 5,747,752 A | 5/1998 | Selinger | |
| 5,796,053 A * | 8/1998 | Shieh | 181/131 |
| 5,813,992 A | 9/1998 | Henwood | |
| 5,920,038 A * | 7/1999 | Foster | 181/131 |
| 5,921,941 A | 7/1999 | Longobardo et al. | |
| 5,932,849 A * | 8/1999 | Dieken | 181/131 |
| 5,945,640 A * | 8/1999 | Rossini et al. | 181/131 |
| 5,949,032 A | 9/1999 | Wurzburger | |
| 6,019,186 A | 2/2000 | Zambrano | |
| 6,019,187 A | 2/2000 | Appavu | |
| 6,041,889 A | 3/2000 | Stark et al. | |
| 6,206,134 B1 * | 3/2001 | Stark et al. | 181/131 |
| 6,244,376 B1 * | 6/2001 | Granzotto | 181/131 |
| 6,378,648 B1 * | 4/2002 | Werblud | 181/131 |
| 6,499,560 B1 | 12/2002 | Land et al. | |
| 6,520,281 B1 | 2/2003 | Deslauriers et al. | |
| 6,523,639 B1 * | 2/2003 | Shieh | 181/131 |
| D475,459 S * | 6/2003 | Wiles | D24/134 |
| 2002/0138015 A1 | 9/2002 | Giroux et al. | |
| 2004/0114767 A1 * | 6/2004 | Tseng | 381/67 |
| 2006/0076184 A1 * | 4/2006 | Robinson | 181/131 |

* cited by examiner

*Primary Examiner*—Edgardo San Martin
(74) *Attorney, Agent, or Firm*—Mathew R. P. Perrone, Jr.; Brie A. Crawford

(57) ABSTRACT

A cover for a stethoscope, and in particular the bell or diaphragm of a stethoscope, has a semi rigid center portion with a flexible skirt extending therefrom. The skirt and the semi rigid center portion terminates in an expandable binding ring, thereby permitting the cove to be applied thereto. The cover may a unitary or a multiple piece.

1 Claim, 7 Drawing Sheets

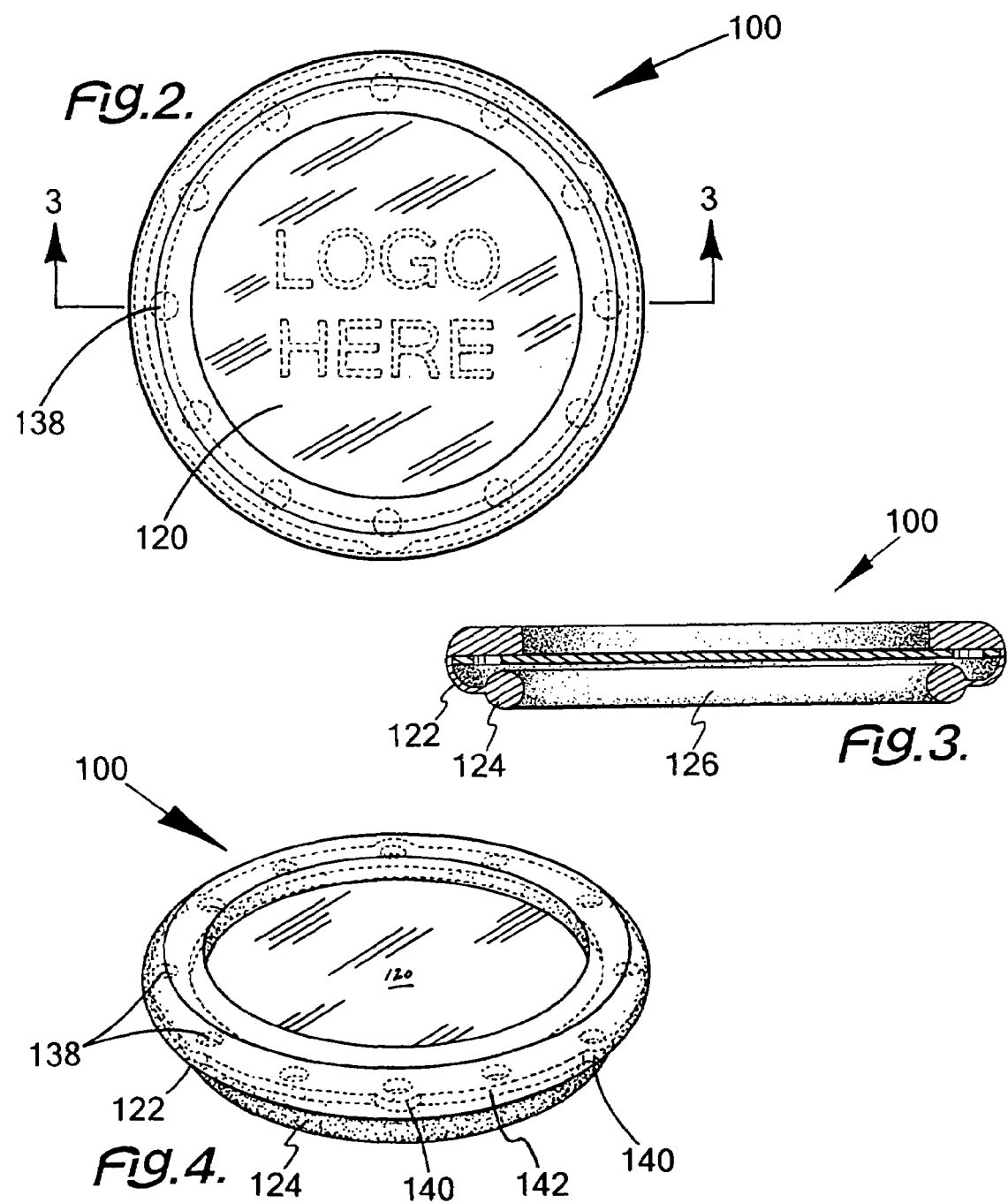

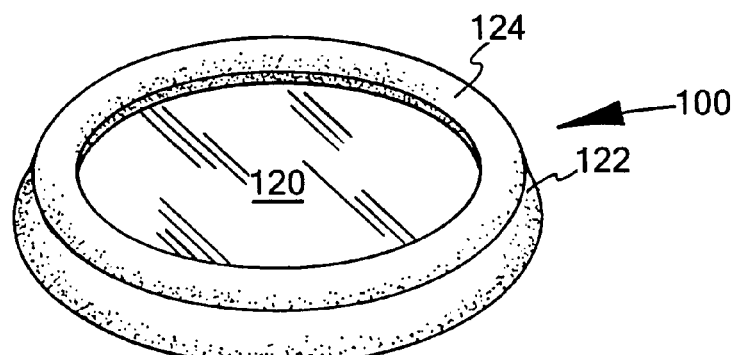
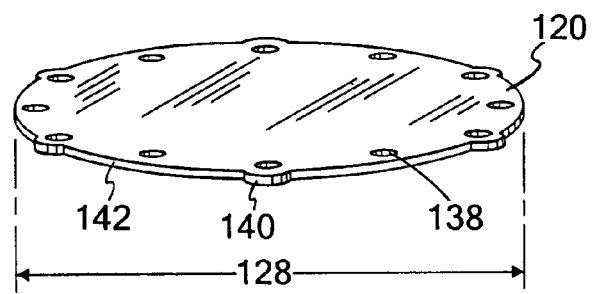
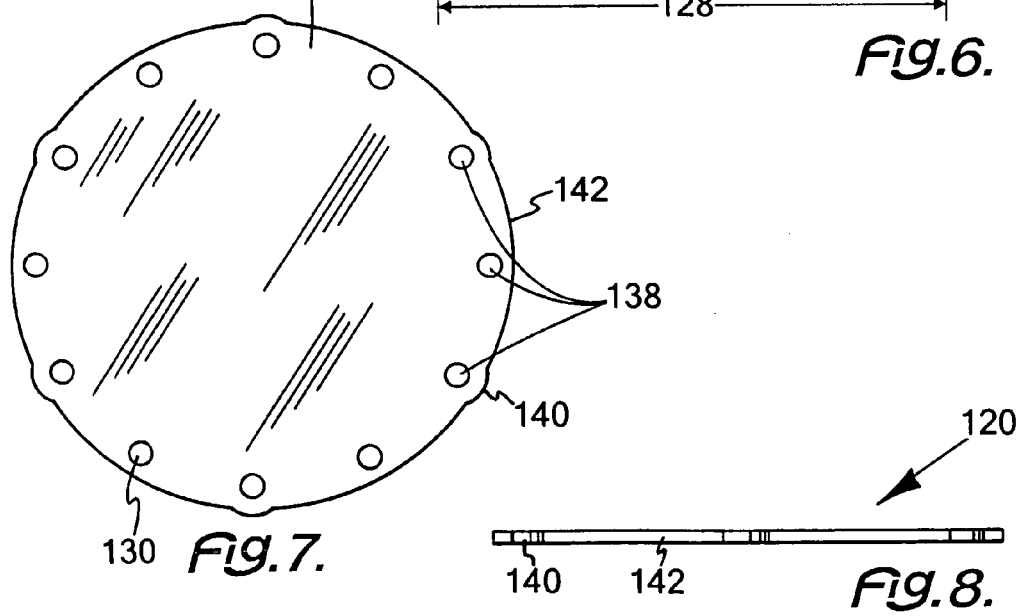

COVER FOR A BELL OR A DIAPHRAGM OF A STETHOSCOPE

This invention relates to a cover for a bell or a diaphragm of a stethoscope, and more particularly, to a cover for a bell or a diaphragm of a stethoscope to maintain the sterility thereof, and provide an entertaining or informing medium.

BACKGROUND OF THE INVENTION

In any area of medicine, a sterile environment is desirable. This requirement applies even to the commonly used stethoscope. Medical personnel use the bell or diaphragm of a stethoscope in order to more clearly hear a person's heart beating or other bodily functions. As the stethoscope is moved from one person to another contamination or disease can also be passed among the various patients.

It is thus very desirable to have a sterile cover for the bell or diaphragm of the stethoscope, which may be attached thereto and used with different patients. Many such covers are known. However, they suffer from a certain difficulty level of attaching or removing the cover efficiently while maintaining the sterility thereof. Also, the cover must not interfere with detection of the bodily sounds.

Such a desired combination of functions has a tendency to interfere with each other. It is therefore desirable to develop a cover, which maximizes the advantage of the cover while maintaining the utility of the stethoscope.

An even further advantage can be obtained if at least part of the cover for the bell or diaphragm of a stethoscope can be decorated in a fashion to entertain or inform the patient. This decoration can be a cartoon, an advertisement, or other suitable decoration. To have a surface suitable for receiving a decoration, while at the same time, adaptable for use on a stethoscope can provide distinct advantages.

SUMMARY OF THE INVENTION

Among the many objectives of this invention is the provision of a cover for a stethoscope, which permits sanitation as well as information.

A further objective of this invention is the provision of a cover for a stethoscope, which protects the bell of the stethoscope.

Yet a further objective of this invention is the provision of a cover for a stethoscope, which protects the diaphram of the stethoscope.

A still further objective of this invention is the provision of a cover for a stethoscope, which is easily installed.

Another objective of this invention is the provision of a cover for a stethoscope, which is easily stored.

Yet another objective of this invention is the provision of a cover for a stethoscope, which is easily removed.

These and other objectives of the invention (which other objectives become clear by consideration of the specification, claims and drawings as a whole) are met by providing a cover for a stethoscope having a semi rigid center portion with a flexible skirt extending therefrom.

BRIEF DESCRIPTION OF THE DRAWINGS

FIG. 2 depicts a top over view of a unitary, temporary sanitary cover 100 of this invention being installed on a stethoscope 110 at the diaphragm 114.

FIG. 3 depicts a cross-section view of the unitary, temporary sanitary cover 100 of this invention.

FIG. 4 depicts a top perspective view of a unitary, temporary sanitary cover 100 of this invention being installed on a stethoscope 110.

FIG. 5 depicts a bottom perspective view of the sanitary device for a temporary sanitary device 100 for a stethoscope 110 of this invention.

FIG. 6 depicts a top perspective view of the semi-rigid disk 120 for a temporary sanitary device 100 for a stethoscope 110 of this invention.

FIG. 7 depicts a top plan view of the semi-rigid disk 120 for the temporary sanitary device 100 for a stethoscope 110 of this invention.

FIG. 8 depicts a side view of the semi-rigid disk 120 for a temporary sanitary device 100 for a stethoscope 110 of this invention.

Throughout the figures of the drawings, where the same part appears in more than one figure of the drawings, the same number is applied thereto.

DESCRIPTION OF THE PREFERRED EMBODIMENTS

In accordance with the present invention, a temporary protective cover for a stethoscope provides sanitary protection and information for patients on which the stethoscope is used. A stethoscope may contain a bell and a diaphragm for listening to various functions of a patient's body. This cover has a flexible, semi-rigid cover adapted to completely protect either the bell or the diaphragm of a stethoscope. The cover is held in place thereover with a flexible skirt extending therefrom and the terminating in an expandable binding ring. The expandable binding ring has a rest diameter less than the diameter of the diaphragm or the bell and an expandable diameter greater than the diameter of the diaphragm or the bell.

So in use, the cover for the stethoscope has the expandable binding ring stretched to a diameter or a size larger than the perimeter or the diameter of the bell or the diaphragm of the stethoscope. The bell or the diaphragm is then inserted into the skirt and adjacent to the flexible cover. Finally, the expandable binding ring is released to its rest diameter. The binding ring and the flexible skirt combined to hold the cover in position.

Any polymer capable of being formed into a light weight, flexible sheet is suitable for forming the stethoscope cover of this invention. The preferred material is a polyolefin. Useful polyolefins include polyethylene, polypropylene, polyvinyl chloride, and copolymers thereof.

Figure 1:
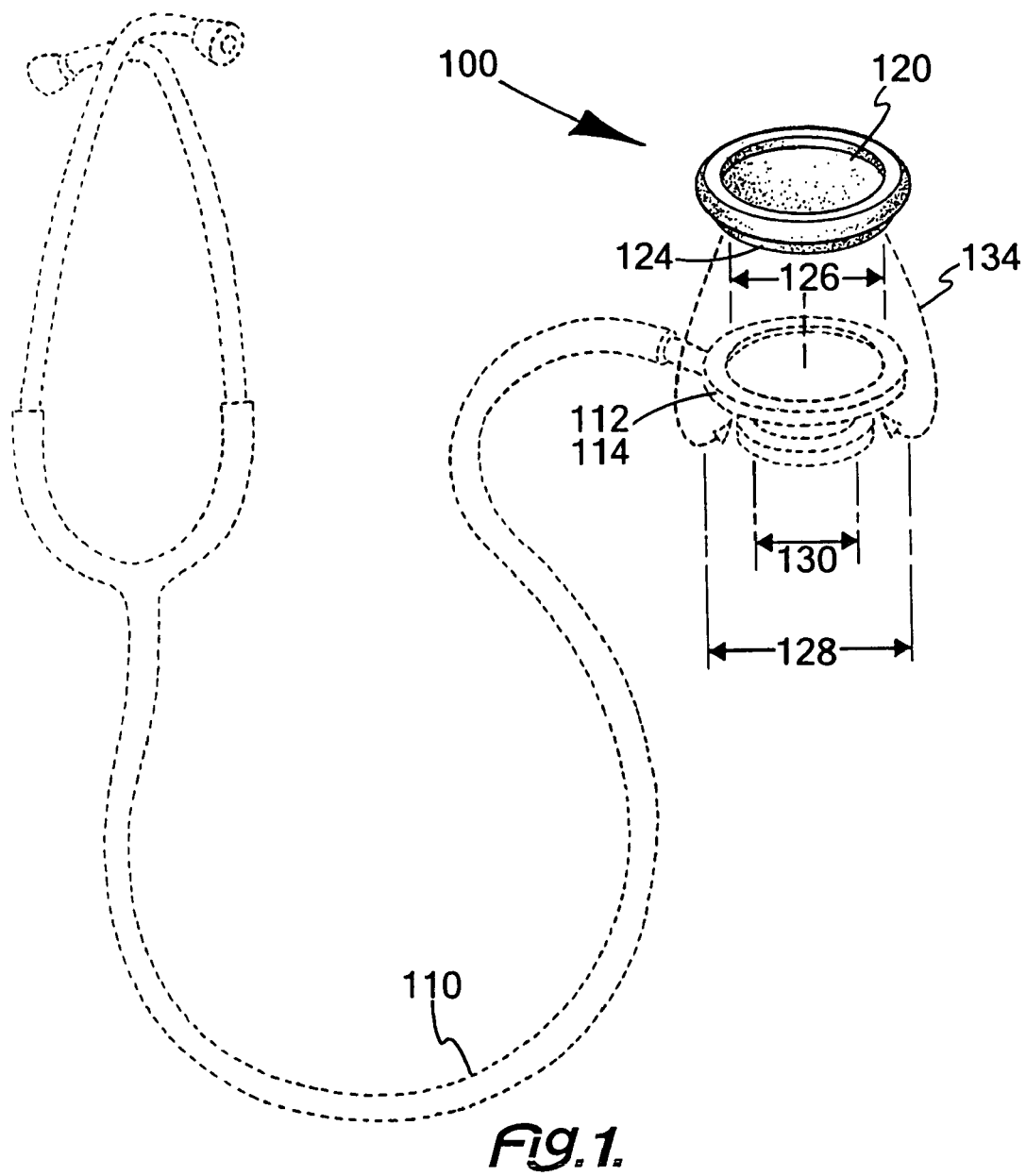
FIG. 1 depicts a top perspective view of a unitary, temporary sanitary cover 100 for a stethoscope 110 of this invention being installed on the stethoscope 110 at the bell 112.

Referring now to FIG. 1, FIG. 2 and FIG. 3; a unitary, temporary sanitary cover 100 for a stethoscope 110 is removably applied to the bell 112 or the diaphragm 114 of stethoscope 110. This unitary, temporary sanitary cover 100 has a flexible, semi-rigid cover 120 centrally located therein to protect either the bell 112 or the diaphragm 114 of the stethoscope 110. The unitary, temporary sanitary cover 100 is held in place thereover with a flexible skirt 122 extending from the edge of the semi-rigid cover 120. Flexible skirt 122 terminates in an expandable binding ring 124, which is oppositely disposed from the cover 120. The expandable binding ring 124 has a rest diameter 126 less than the flat diameter 128 of the diaphragm 114 or the hollow diameter 130 the bell 112.

As the expandable diameter 134 of the expandable binding ring 124 can easily reach any diameter greater than the flat diameter 128 of the diaphragm 114 or the hollow diameter 130 the bell 112, the expandable binding ring 124 may receive either flat diameter 128 or hollow diameter 130. Thus, semi-rigid cover 120 of the unitary, temporary sanitary cover 100 is releasably secured as desired over the bell 112 or the diaphragm 114 of the stethoscope 110.

Adding FIG. 4, FIG. 5, FIG. 6, FIG. 7, and FIG. 8 to the consideration, the unitary, temporary sanitary cover 100 for the stethoscope 110 has the expandable binding ring 124 to permit covering of the diaphragm 114 or the bell 112 of the stethoscope 110. As the bell 112 or the diaphragm 114 is then inserted into the flexible skirt 122 and adjacent to the semi rigid cover 120. Finally, the expandable binding ring 124 is released to its rest diameter. The binding ring 124 and the flexible skirt 122 combine to hold the semi rigid cover 120 in position on the stethoscope 110.

The larger semi rigid cover 120 has a printable surface 136 capable of having advertising or decorations printed or otherwise set thereon as in FIG. 1. Such decorations, such as cartoon characters, can entertain a patient. The advertising, such as drugs or healthcare tips, can inform a patient.

Furthermore, the semi rigid cover 120 has a plurality of cover apertures 138 around the edge thereof. When the over molding of the skirt 122 to the semi rigid cover 120, cover apertures 138 near the edge thereof permit a stronger bond of the skirt 122 thereto. Likewise, cover ridges 140 in the edge 142 of semi rigid cover 120 assist in the bonding therebetween during the over molding process.

Figure 9:
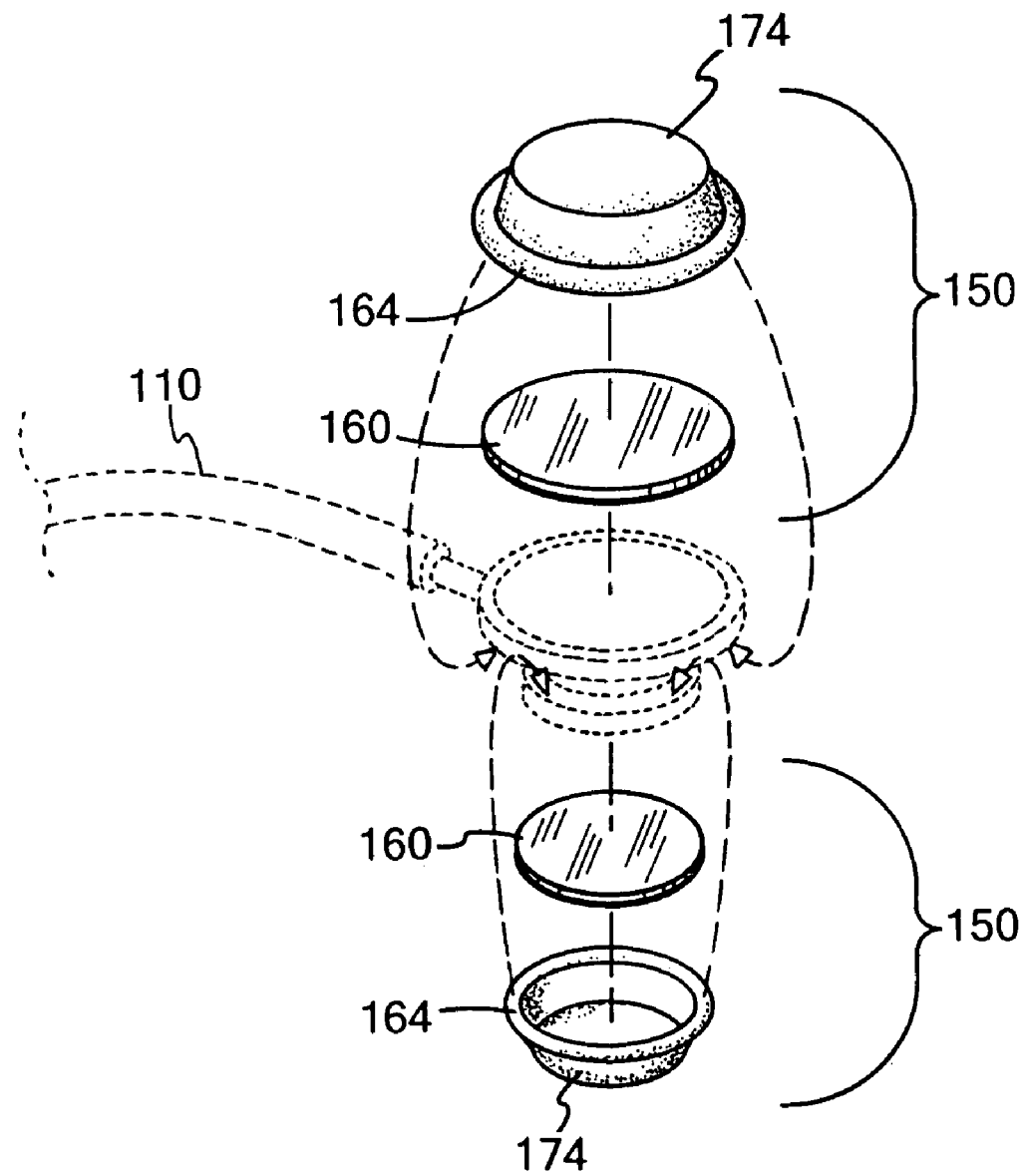
FIG. 9 depicts a top, exploded perspective view of a two piece temporary sanitary device 150 for a stethoscope 110 of this invention being installed on the stethoscope 110.
Figure 10:
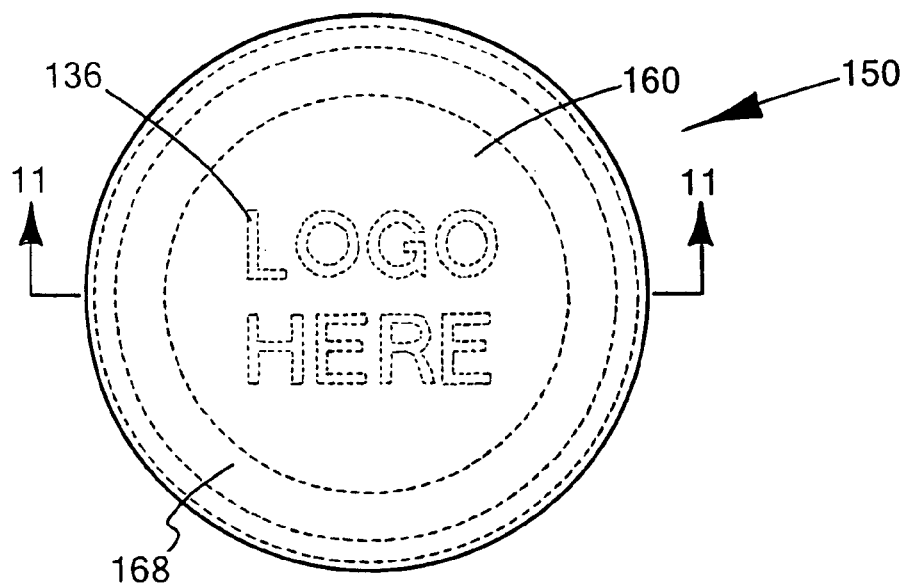
FIG. 10 depicts a top plan view of a two piece temporary sanitary device 150 for a stethoscope 110.
Figure 11:
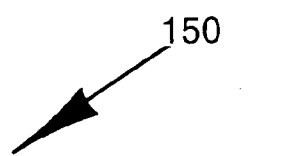
FIG. 11 depicts a side view of a two piece temporary sanitary device 150 for a stethoscope 110 of this invention in partial cross-section.
Figure 12:
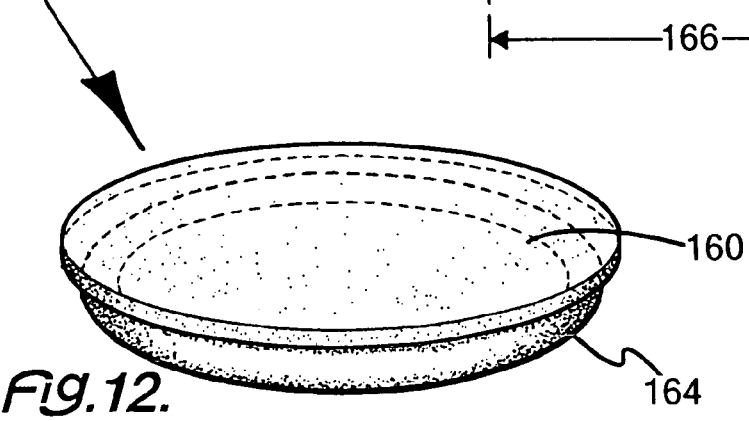
FIG. 12 depicts a top, expanded perspective view of the two piece temporary sanitary device 150 for a stethoscope 110 of this invention.
Figure 13:
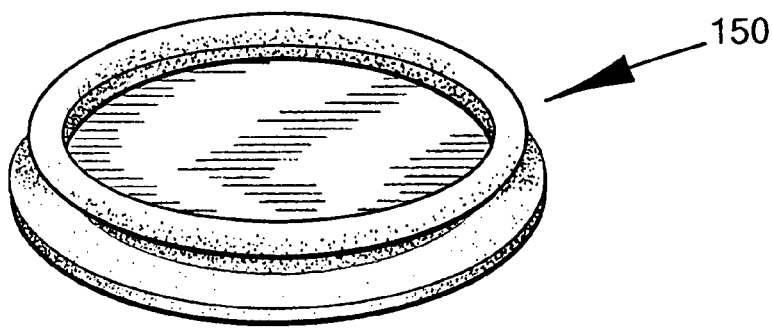
FIG. 13 depicts a bottom perspective view of the sanitary device for a two piece temporary sanitary device 150 for a stethoscope 110 of this invention.
Figure 14:
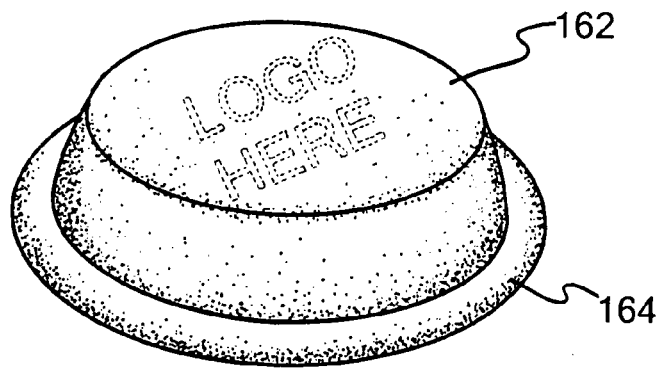
FIG. 14 depicts a top, perspective view of the temporary sanitary device 100 for a stethoscope 110 of this invention.
Figure 15:
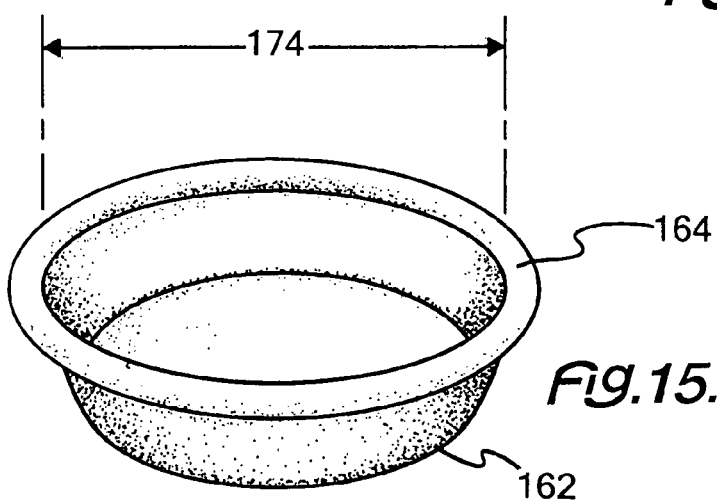
FIG. 15 depicts a bottom perspective view of the two piece temporary sanitary device 150 for a stethoscope 110 of this invention.

Referring now to FIG. 9, FIG. 10 and FIG. 11; a two-piece temporary sanitary device 100 for a stethoscope 110 is removably applied to the bell 112 or the diaphragm 114 of stethoscope 110. This two-piece temporary sanitary device 150 has a flexible, semi-rigid disk 120 centrally located therein to protect either the bell 112 or the diaphragm 114 of the stethoscope 110. The two piece temporary sanitary device 150 is held in place thereover with a flexible, stretchable cover 162 extending from the edge of the semi-rigid disk 160. Stretchable cover 162 terminates in an expandable binding ring 164. The expandable binding ring 164 has a rest diameter 166 less than the flat diameter 128 (FIG. 9) of the diaphragm 114 or the hollow diameter 130 of the bell 112.

Semi-rigid disk 160 also has a printable surface 136 informative or entertaining purposes. Similar information may be placed thereon.

As the expandable diameter of the expandable binding ring 164 can easily reach any diameter greater than the flat diameter 128 of the diaphragm 114 or the hollow diameter 130 the bell 112. The expandable binding ring 164 may receive either flat diameter 128 or hollow diameter 130. Thus, plastic disk 160 of the two-piece temporary sanitary device 100 is releasably secured as desired over the bell 112 or the diaphragm 114 of the stethoscope 110.

Adding FIG. 12, FIG. 13, FIG. 14, and FIG. 15 to the consideration, the two-piece temporary sanitary device 150 for the stethoscope 110 has the expandable binding ring 164 to permit covering of the bell 112 or the diaphragm 114 of the stethoscope 110. As the bell 112 or the diaphragm 114 is then inserted into the flexible, stretchable cover 162 and adjacent to the semi rigid disk 162. Finally, the expandable binding ring 164 is released to its rest diameter 174. The binding ring 164 and the flexible, stretchable cover 162 combine to hold the separable plastic disk 160 in position on either the bell 112 or the diaphragm 114 of the stethoscope 110.

Figure 16:
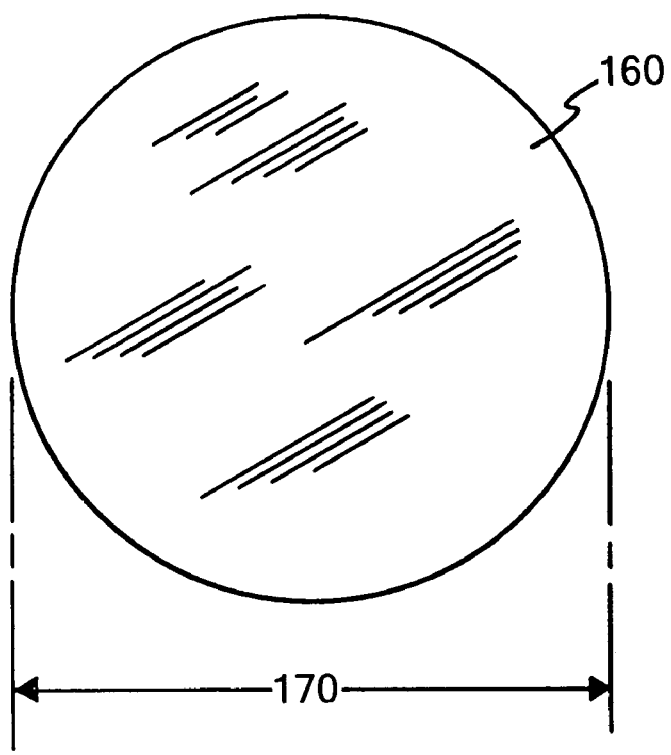
FIG. 16 depicts a top plan view of semi rigid disc 120 for the temporary sanitary device 100 for a stethoscope 110 of this invention.
Figure 17:
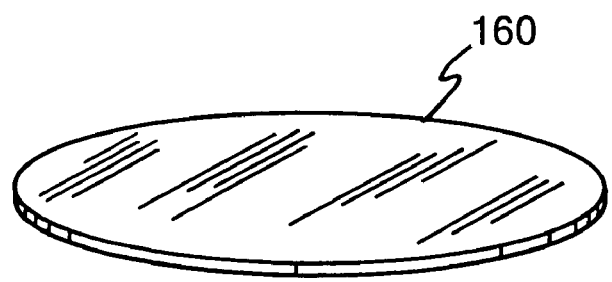
FIG. 17 depicts a top perspective view of semi rigid disc 120 for the temporary sanitary device 100 for a stethoscope 110 of this invention.

Finally considering FIG. 16 and FIG. 17, the larger separable plastic disk 160, within a disk diameter, has a printable surface 136 capable of having advertising or decorations printed or otherwise set thereon. Diameter 136 is at of sufficient size for semi rigid disk 120 to cover bell 112 or diaphragm 114, while permitting the desired bodily sounds to pass therethrough and be interpreted by medical personnel. Such decorations, such as cartoon characters, can entertain a patient. The advertising, such as drugs or healthcare tips, can inform a patient.

This application—taken as a whole with the abstract, specification, claims, and drawings being combined—provides sufficient information for a person having ordinary skill in the art to practice the invention as disclosed and claimed herein. Any measures necessary to practice this invention are well within the skill of a person having ordinary skill in this art after that person has made a careful study of this disclosure.

Because of this disclosure and solely because of this disclosure, modification of this method and device can become clear to a person having ordinary skill in this particular art. Such modifications are clearly covered by this disclosure.

What is claimed and sought to be protected by Letters Patent of the United States is:

1. A unitary sanitary device for a stethoscope comprising:
    (a) the unitary sanitary device having a disk;
    (b) a flexible skirt extending from the disk;
    (c) an expandable binding ring combining with the flexible skirt to hold the disk in place;
    (d) the expandable binding ring having a rest diameter less than either a diaphragm for the stethoscope or a bell for the stethoscope;
    (e) the expandable binding ring being releasably expandable to a binding ring diameter;
    (f) the binding ring diameter being greater than either a diameter for a diaphragm on the stethoscope or a diameter for a bell on the stethoscope;
    (g) the disk being made of a light weight and flexible material;
    (h) the light weight and flexible material being polyethylene, polypropylene, polyvinyl chloride, or copolymers thereof;
    (i) the disk containing disk apertures to permit a stronger bond to the flexible skirt; and
    (j) the disk containing disk ridges in an edge of the disk.

* * * * *